US010145824B2

(12) United States Patent
Liu

(10) Patent No.: US 10,145,824 B2
(45) Date of Patent: *Dec. 4, 2018

(54) ANALYTICAL METHODS FOR ANALYZING AND DETERMINING IMPURITIES IN DIANHYDROGALACTITOL

(71) Applicant: DelMar Pharmaceuticals, Inc., Vancouver (CA)

(72) Inventor: Xiaoyun Liu, Vancouver (CA)

(73) Assignee: Del Mar Pharmaceuticals (BC) Ltd., Vancouver (CA)

( * ) Notice: Subject to any disclaimer, the term of this patent is extended or adjusted under 35 U.S.C. 154(b) by 893 days.

This patent is subject to a terminal disclaimer.

(21) Appl. No.: 14/380,924

(22) PCT Filed: Feb. 26, 2013

(86) PCT No.: PCT/IB2013/000793
§ 371 (c)(1),
(2) Date: Aug. 25, 2014

(87) PCT Pub. No.: WO2013/128285
PCT Pub. Date: Sep. 6, 2013

(65) Prior Publication Data
US 2015/0027206 A1 Jan. 29, 2015

Related U.S. Application Data

(60) Provisional application No. 61/603,464, filed on Feb. 27, 2012.

(51) Int. Cl.
| | | |
|---|---|---|
| *G01N 30/88* | (2006.01) | |
| *G01N 33/15* | (2006.01) | |
| *G01N 30/06* | (2006.01) | |
| *G01N 30/72* | (2006.01) | |
| *G01N 30/74* | (2006.01) | |
| *G01N 21/49* | (2006.01) | |
| *G01N 30/02* | (2006.01) | |

(52) U.S. Cl.
CPC .......... *G01N 30/88* (2013.01); *G01N 21/49* (2013.01); *G01N 30/06* (2013.01); *G01N 30/7233* (2013.01); *G01N 33/15* (2013.01); *G01N 30/74* (2013.01); *G01N 2030/027* (2013.01); *G01N 2030/743* (2013.01); *G01N 2030/8813* (2013.01); *G01N 2030/8872* (2013.01); *Y10T 436/142222* (2015.01); *Y10T 436/203332* (2015.01)

(58) Field of Classification Search
CPC .............. G01N 30/3088; G01N 30/74; G01N 30/7233; G01N 30/06; G01N 2030/743; G01N 2030/027; G01N 2030/8872; G01N 33/15; G01N 21/49
See application file for complete search history.

(56) References Cited

U.S. PATENT DOCUMENTS

| | | | |
|---|---|---|---|
| 7,157,079 B2 | 1/2007 | Nielsen et al. | |
| 9,029,164 B2 * | 5/2015 | Lu ........................ | G01N 33/15 |
| | | | 424/649 |
| 9,759,698 B2 * | 9/2017 | Liu ....................... | G01N 21/49 |
| 2014/0017798 A1 | 1/2014 | Yu | |

FOREIGN PATENT DOCUMENTS

| | | |
|---|---|---|
| CL | 2014002276 A1 | 12/2014 |
| JP | H04297868 A | 10/1992 |
| JP | H09229920 A | 9/1997 |
| JP | 2000506969 A | 6/2000 |
| JP | 2004517131 A | 6/2004 |
| JP | 2004294384 A | 10/2004 |
| JP | 2007538251 A | 12/2007 |
| JP | 2008076340 A | 4/2008 |
| JP | 2008518881 A | 6/2008 |
| WO | 9731865 A1 | 9/1997 |
| WO | 0042225 A1 | 7/2000 |
| WO | 02055016 A2 | 7/2002 |
| WO | 2005007122 A2 | 1/2005 |
| WO | 2005114171 A2 | 12/2005 |
| WO | 2011092120 A1 | 8/2011 |
| WO | 2012/024368 A2 | 2/2012 |

(Continued)

OTHER PUBLICATIONS

Boselli, E. et al. "Determination of phospholipid molecular species in pork meat by high performance liquid chromatography—tandem mass spectrometry and evaporative light scattering detection." Meat Science (2008) 78 305-313.*
Institoris, L. et al. "Investigation into the Correlation of Cytostatic Activity with the in vitro Diepoxide Formation on some Terminally Substituted Hexitols." Neoplasma (1970) 17 15-24.*
Jarman, M. et al. "The formation of epoxides from substituted hexitols." Carbohydrate Research (1969) 9 139-147.*
Simon, K. et al. "The Crystal and Molecular Structure of Dibromodulcitol C6H12OaBr2 and Dichloroduleitol C6H1204C12." Acta Crysta. (1971) B27 806-815.*

(Continued)

*Primary Examiner* — Christopher Adam Hixson
(74) *Attorney, Agent, or Firm* — Christensen O'Connor Johnson Kindness PLLC

(57) ABSTRACT

An improved analytical method for analysis of dianhydrogalactitol preparations provides a method for determining the purity of dianhydrogalactitol and detecting impurities in preparations of dianhydrogalactitol, as well as identifying any such impurities. The method employs high performance liquid chromatography (HPLC), in particular, HPLC with refractive index (RI) detection; the HPLC can be followed by tandem mass spectroscopy. The method can further comprise the step of performing preparative HPLC collection of at least one specific substance peak present in a preparation of dianhydrogalactitol.

42 Claims, 2 Drawing Sheets

(56) References Cited

FOREIGN PATENT DOCUMENTS

WO     2012024368 A2     2/2012
WO     2013/128285 A2     9/2013

OTHER PUBLICATIONS

Spanos, George A. et al. "High-Performance Liquid Chromatography with Light-Scattering Detection and Desorption Chemical-Ionization Tandem Mass Spectrometry of Milk Fat Triacylglycerols." Lipids (1995) 30 85-90.*
McCrossen et al., "Comparison of LC detection methods in the investigation of non-UV detectable organic impurities in a drug substance", Journal of Pharmaceutical and Biomedical Analysis, Jul. 1998, vol. 17, No. 3, 18 Pages.
Caamano et al., "Improved RPLC determination of acyclovir using hexylamine as silanol masking agent", Journal of Pharmaceutical and Biomedical Analysis, Nov. 2, 1999, vol. 21, No. 3, 6 Pages.
European Office Action for related European Patent Application No. 13754722.0-1554 dated Oct. 20, 2015, 7 Pages.
McCrossen et al., "Comparison of LC detection methods in the investigation of non-UV detectable organic impurities in a drug substance", Journal of Pharmaceutical and Biomedical Analysis, Jul. 1, 1998, vol. 17, No. 3, 18 Pages.
Caamano et al., "Improved RPLC determination of acyclovir using hexylamine as silanol masking agent", Journal of Pharmaceutical and Biomedical Analysis, Jan. 1, 1999, vol. 21, No. 3, 6 Pages.
R. N. Rao et al., "An Overview of the Recent Trends in Development of HPLC Methods for Determination of Impurities in Drugs," J. Pharm. Biomed. Anal. 33: 335-377 (2003).
D. Bartos et al., "Recent Advances in the Impurity Profiling of Drugs," Curr. Pharm. Anal. 4: 215-230 (2008).
M.D. Lantz et al., "Simultaneous Resolution and Detection of a Drug Substance, Impurities, and Counter Ion Using a Mixed-Mode HPLC Column with Evaporative Light Scattering Detection," J. Liquid Chromatography Rel. Tech. 20: 1409-1422 (1997).
Terada et al., "How to Use Evaporative Light Scattering Detector Effectively", Chromatography, 2011, vol. 32, No. 3, with English-language summary, pp. 141-152.
Office Action and Analysis by Mexican Associate dated Apr. 2, 2018, issued in Mexican Application No. MX/a/2014/010312, Filed Feb. 26, 2013, 6 pages.
Office Action dated Jan. 18, 2018, issued in corresponding Chilean Application No. 201402276, Filed Aug. 27, 2014, 9 pages.
Office Action dated Jan. 11, 2018, issued in corresponding Chilean Application No. 201601197, Filed May 18, 2016, 21 pages.
"From Microanalysis to Plant-Scale Purification," Bioseparation Products Catalog, YMC Co., Ltd., Kyoto, Japan, Nov. 2015, 24 pages.
"Guidance for Industry Q2B Validation of Analytical Procedures: Methodology," U.S. Department of Health and Human Services, Food and Drug Administration, Nov. 2016, 13 pages.
Guzzetta, A., "Reverse Phase HPLC Basics for LC/MS," IonSource, Jul. 2001, 9 pages.
"2424 Evaporative Light Scattering Detector, Operator's Guide," Waters Corporation, 2009, 196 pages.

* cited by examiner

ANALYTICAL METHODS FOR ANALYZING AND DETERMINING IMPURITIES IN DIANHYDROGALACTITOL

CROSS-REFERENCES

This application claims the benefit of U.S. Provisional Patent Application Ser. No. 61/603,464, entitled "Improved Analytical Methods for Analyzing and Determining Impurities in Dianhydrogalactitol" by Xiaoyun Lu, filed Feb. 27, 2012, the contents of which are incorporated herein in their entirety by this reference.

FIELD OF THE INVENTION

This invention is directed to improved analytical methods for dianhydrogalactitol, especially involving high performance liquid chromatography (HPLC).

BACKGROUND OF THE INVENTION

Dianhydrogalactitol (1,2:5,6 dianhydrogalactitol or DAG) is one of a number of hexitols or hexitol derivatives having significant pharmacological activity, including chemotherapeutic activity. In particular, dianhydrogalactitol has been suggested for use in chemotherapy, such as in U.S. Pat. No. 7,157,079 to Nielsen et al., incorporated herein by this reference.

Dianhydrogalactitol has activity against a number of neoplasms. However, if dianhydrogalactitol is to be used successfully as a therapeutic agent, an extremely high degree of purity and the removal of impurities is essential. The presence of impurities can lead to undesirable side effects. One example occurred a number of years ago, when impurities present in a batch of the amino acid tryptophan, a normal constituent of protein, were responsible for a significant outbreak of eosinophilia-myalgia syndrome, which caused a large number of cases of permanent disability and at least 37 deaths. This is particularly important if the therapeutic agent such as dianhydrogalactitol is to be employed in patients with compromised immune systems or liver or kidney dysfunction, or in elderly patients. Such patients may experience a greater incidence of undesirable side effects owing to their sensitivity to contaminants.

One of the impurities found in preparations of dianhydrogalactitol is dulcitol. Other impurities exist in preparations of dianhydrogalactitol as well, depending on their method of preparation.

Therefore, there is a need for improved analytical methods to detect impurities and degradation products in preparations of dianhydrogalactitol to provide preparations of greater purity that are less likely to induce side effects when dianhydrogalactitol is administered for therapeutic purposes.

SUMMARY OF THE INVENTION

An improved analytical method for determining the purity of dianhydrogalactitol and detecting impurities and degradation products in preparations of dianhydrogalactitol that meets these needs is described herein.

In general, this analytical method employs high performance liquid chromatography (HPLC), in particular, HPLC with refractive index (RI) detection.

In one alternative, an analytical method for analyzing the presence and quantity of impurities present in a preparation of dianhydrogalactitol comprises the steps of:

(1) analyzing a preparation of dianhydrogalactitol by subjecting the preparation to high performance liquid chromatography using elution with a mobile phase gradient to separate dianhydrogalactitol from dulcitol and other contaminants of the preparation; and (2) determining the relative concentration of one or more peaks resolved by high performance liquid chromatography that represent compounds other than dianhydrogalactitol itself.

The compounds other than dianhydrogalactitol itself can be at least one of: (1) dulcitol; (2) an impurity other than dulcitol; and (3) a degradation product of dianhydrogalactitol.

In one alternative of this method, elution is with a gradient of NaOH from about 2.5 mM to about 0.1 mM. Preferably, elution is with a gradient of NaOH from about 1.5 mM to about 0.1 mM. More preferably, elution is with a gradient of NaOH from about 1 mM to about 0.1 mM.

In another alternative of this method, elution is with a gradient of a combination of ammonium hydroxide and a volatile ammonium salt selected from the group consisting of ammonium formate and ammonium acetate and the total concentration of the ammonium formate and ammonium acetate is from about 2.5 mM to about 0.1 mM. Preferably, the total concentration of the ammonium hydroxide and the volatile ammonium salt selected from the group consisting of ammonium formate and ammonium acetate is from about 1.5 mM to about 0.1 mM. More preferably, the total concentration of the ammonium hydroxide and the volatile ammonium salt selected from the group consisting of ammonium formate and ammonium acetate is from about 1 mM to about 0.1 mM. Typically, the proportion of ammonium hydroxide and the volatile ammonium salt selected from the group consisting of ammonium formate and ammonium acetate is varied from about 100:1 at the beginning of elution to about 1:100 at the end of elution.

Typically, in this method, the step of determining the relative concentration of one or more peaks resolved by high performance liquid chromatography that represent compounds other than dianhydrogalactitol itself is performed by evaporative light scattering detection. Typically, the evaporative light scattering detection is compatible with electrospray LC/MS. Typically, the evaporative light scattering detection comprises post-column addition of a volatile solvent to enhance evaporation of the 100% aqueous mobile phase. Typically, the volatile solvent is selected from the group consisting of methanol, ethanol, isopropanol, and acetonitrile.

In one alternative, an electrospray tandem mass spectrometer is installed and connected on-line to an HPLC system with ELSD. Typically, in this alternative, mass spectral data providing chemical information for each of the impurities that may be present in a preparation of dianhydrogalactitol is collected. Also, typically, in this alternative, tandem mass spectral data providing structural information for each of the impurities that may be present in a preparation of dianhydrogalactitol is collected.

The method can further comprise the step of performing preparative HPLC collection of at least one specific substance peak present in a preparation of dianhydrogalactitol. The at last one substance peak present in the preparation of dianhydrogalactitol can be an impurity.

In another alternative, instead of gradient elution, isocratic elution can be used. When isocratic elution is used, in general, the method comprises the steps of:

(1) analyzing a preparation of dianhydrogalactitol by subjecting the preparation to high performance liquid chromatography using elution with an isocratic mobile phase to separate dianhydrogalactitol from dulcitol and other contaminants of the preparation; and (2) determining the relative concentration of one or more peaks resolved by high performance liquid chromatography that represent compounds other than dianhydrogalactitol itself.

In one alternative, when isocratic elution is used, the isocratic mobile phase is NaOH, and the concentration of NaOH is from about 5 mM to 0.1 mM. Preferably, the concentration of NaOH is from about 2.5 mM to about 0.1 mM. More preferably, the concentration of NaOH is about 1 mM.

In another alternative, when isocratic elution is used, the isocratic mobile phase is a combination of ammonium hydroxide and a volatile ammonium salt selected from the group consisting of ammonium formate and ammonium acetate and the total concentration of the ammonium hydroxide and the volatile ammonium salt selected from the group consisting of ammonium formate and ammonium acetate is from about 5 mM to 0.1 mM. Preferably, the total concentration of the ammonium hydroxide and the volatile ammonium acetate is from about 2.5 mM to about 0.1 mM. More preferably, the total concentration of the ammonium hydroxide and the volatile ammonium salt selected from the group consisting of ammonium formate and ammonium acetate is about 1 mM. Typically, the proportion of ammonium hydroxide and the volatile ammonium salt selected from the group consisting of ammonium formate and ammonium acetate is about 50:50.

Typically, in this alternative, the step of determining the relative concentration of one or more peaks resolved by high performance liquid chromatography that represent compounds other than dianhydrogalactitol itself is performed by evaporative light scattering detection (ELSD), as described above. Typically, the evaporative light scattering detection is compatible with electrospray LC/MS. Typically, the evaporative light scattering detection comprises post-column addition of a volatile solvent to enhance evaporation of the 100% aqueous mobile phase. Typically, the volatile solvent is selected from the group consisting of methanol, ethanol, isopropanol, and acetonitrile.

In this alternative as well, an electrospray tandem mass spectrometer can be installed and connected on-line to an HPLC system with ELSD. Typically, in this alternative, mass spectral data providing chemical information for each of the impurities that may be present in a preparation of dianhydrogalactitol is collected. Also, typically, in this alternative, tandem mass spectral data providing structural information for each of the impurities that may be present in a preparation of dianhydrogalactitol is collected.

This alternative of a method according to the present invention can further comprise the step of performing preparative HPLC collection of at least one specific substance peak present in a preparation of dianhydrogalactitol. The at last one substance peak present in the preparation of dianhydrogalactitol can be an impurity.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

This invention is directed to improved analytical methods for determining the purity of dianhydrogalactitol and determining the existence and concentration of impurities present in preparations of dianhydrogalactitol.

The structure of dianhydrogalactitol is shown below in Formula (I).

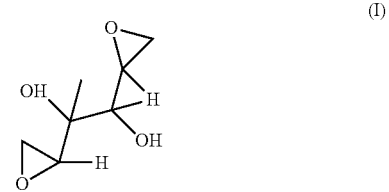

One of the significant impurities present in dianhydrogalactitol preparations is dulcitol. The structure of dulcitol is shown below in Formula (II). Other impurities are known to exist in dianhydrogalactitol preparations.

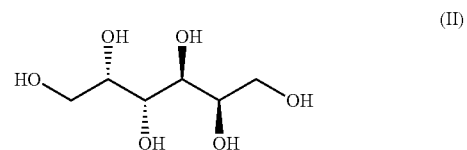 [SMILES: OC[C@@H](O)[C@H](O)[C@H](O)[C@@H](O)CO]

An improved method of analyzing dianhydrogalactitol preparations is based on HPLC (high performance liquid chromatography) with evaporative light scattering detection (ELSD). In one alternative, to detect and identify all significant components present in such dianhydrogalactitol preparations, HPLC is combined with mass spectroscopy (MS).

The theory and practice of HPLC are described in L. R. Snyder et al., "Introduction to Modern Liquid Chromatography" (3$^{rd}$ ed., John Wiley & Sons, New York, 2009). The theory and practice of MS are described in E. de Hoffmann & V. Stroobant, "Mass Spectroscopy: Principles and Applications" (3$^{rd}$ ed., John Wiley & Sons, New York, 2007).

Figure 1:
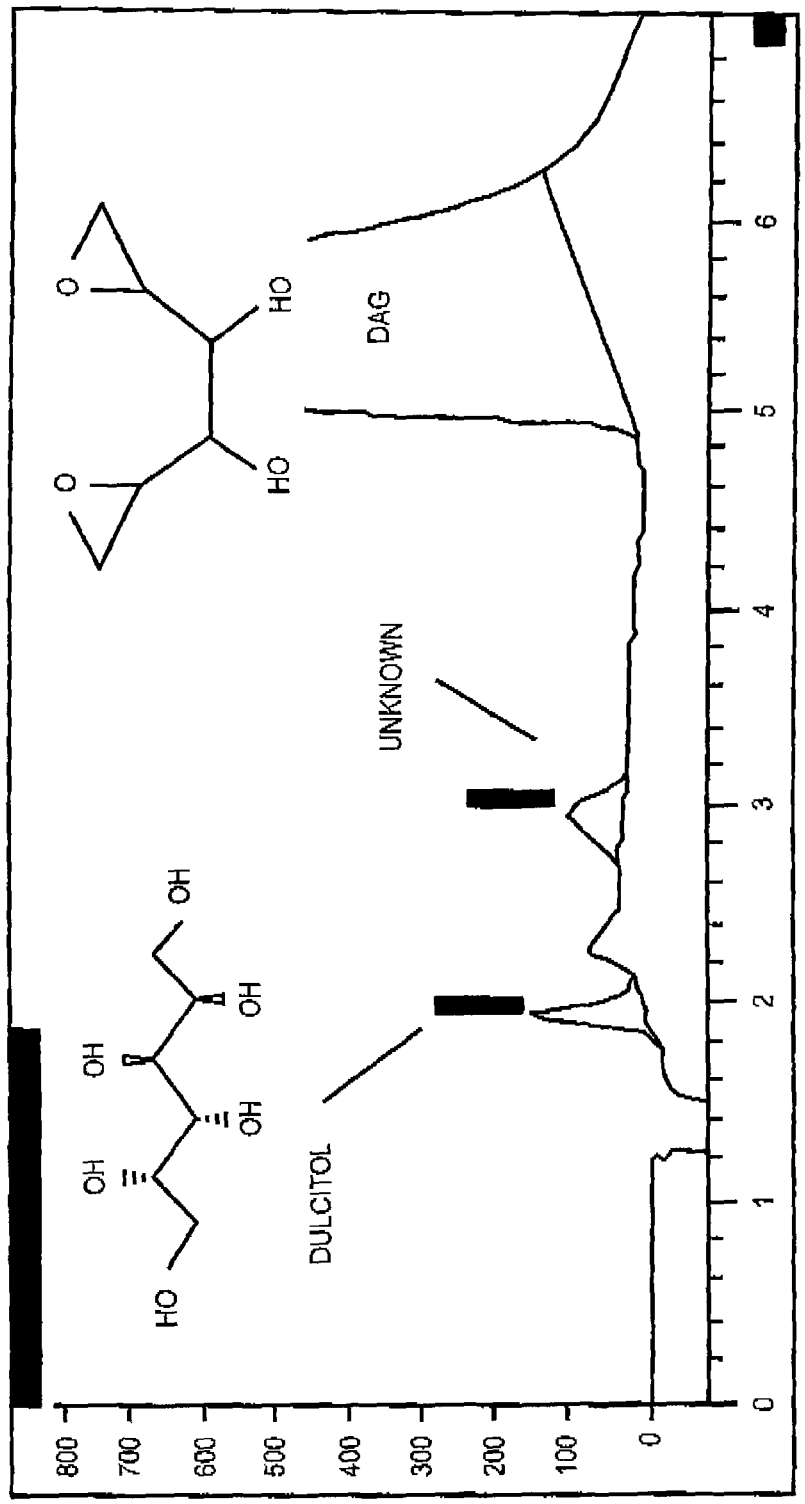
FIG. 1 is a representative HPLC/RI chromatogram of a preparation of dianhydrogalactitol, showing resolution of dulcitol and an unknown related substance at RRT~0.6 in the bulk drug and drug product.

The HPLC method has demonstrated resolution of a synthetic intermediate, dulcitol, in preparations of dianhydrogalacitol, in addition to resolution of an unknown related substance observed at RRT 0.6 (FIG. 1). FIG. 1 is a representative HPLC/RI chromatogram of a preparation of dianhydrogalactitol, showing resolution of dulcitol and an unknown related substance at RRT~0.6 in the bulk drug and drug product. Representative HLPC chromatograms showing resolution of dianhydrogalactitol and dulcitol in a standard, and, for comparison, a water blank, are shown in FIG.

Figure 2:
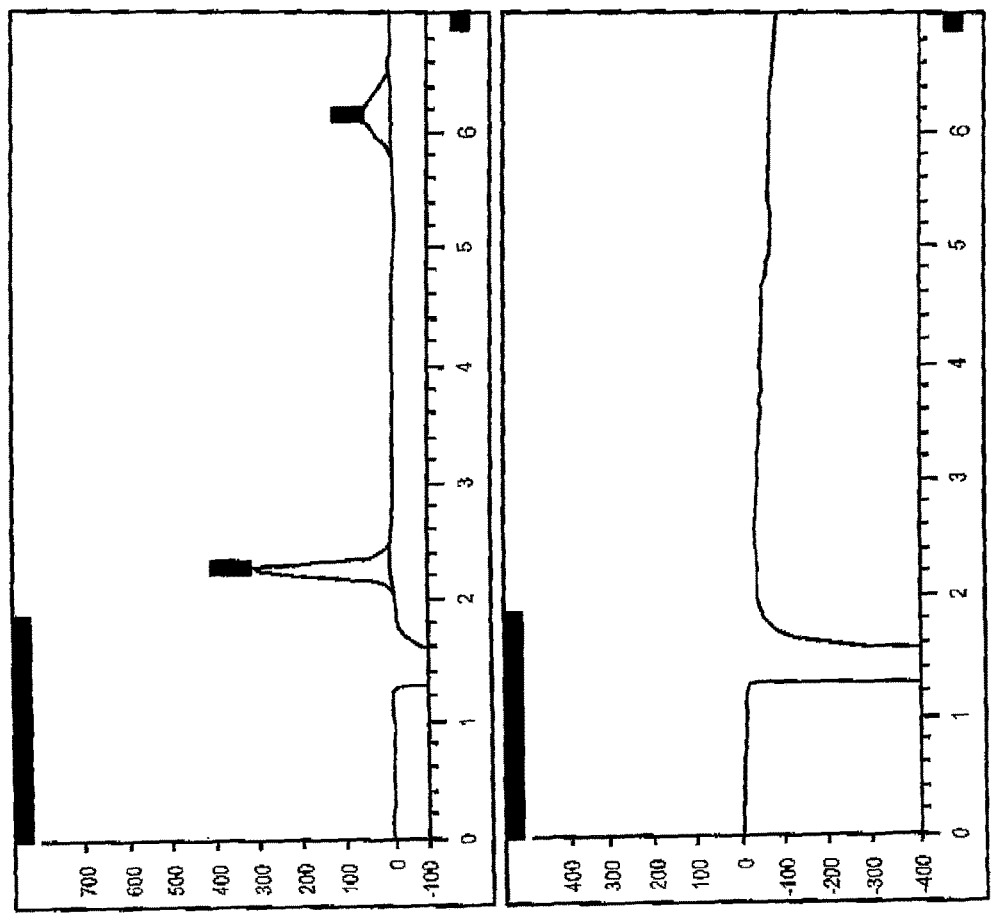
FIG. 2 shows representative HLPC chromatograms showing resolution of dianhydrogalactitol and dulcitol in a standard, and, for comparison, a water blank; li FIG. 2, the dianhydrogalactitol-dulcitol standard is shown in the top panel, and the water blank is shown in the bottom panel.

2. In FIG. 2, the dianhydrogalactitol-dulcitol standard is shown in the top panel, and the water blank is shown in the bottom panel.

The present application describes improved HPLC chromatographic conditions for resolution of potentially co-eluting substances. A thermally stressed dianhydrogalactitol product sample is evaluated to provide confirmation of the chromatographic conditions appropriate for resolution of dulcitol and other related impurities and degradation products. Subsequently, LC/MS and LC/MS/MS is performed to characterize the unknown DAG-related substance at RRT~0.6 to provide mass spectral characterization and determination of the chemical structure of this unidentified component.

Dianhydrogalactitol and its related substances can be analyzed by HPLC conditions involving isocratic elution with a 50 mM NaOH mobile phase. In an improvement on these conditions, employed as part of the method disclosed herein, a gradient mobile phase is employed. One alternative is the use of NaOH in a concentration gradient. If NaOH is employed in a concentration gradient, typically elution is with a gradient of NaOH from about 2.5 mM to about 0.1 mM. Preferably, elution is with a gradient of NaOH from about 1.5 mM to about 0.1 mM. More preferably, elution is with a gradient of NaOH from about 1 mM to about 0.1 mM.

In another alternative, a combination of ammonium hydroxide and a volatile ammonium salt selected from the group consisting of ammonium formate and ammonium acetate can be used as eluant. In this alternative, the total concentration of the ammonium formate and ammonium acetate is from about 2.5 mM to about 0.1 mM. Preferably, the total concentration of the ammonium hydroxide and the volatile ammonium salt selected from the group consisting of ammonium formate and ammonium acetate is from about 1.5 mM to about 0.1 mM. More preferably, the total concentration of the ammonium hydroxide and the volatile ammonium salt selected from the group consisting of ammonium formate and ammonium acetate is from about 1 mM to about 0.1 mM. Typically, the proportion of ammonium hydroxide and the volatile ammonium salt selected from the group consisting of ammonium formate and ammonium acetate is varied from about 100:1 at the beginning of elution to about 1:100 at the end of elution.

Other gradient elution schemes are known in the art.

Typically, in HPLC analytical methods according to the present invention, detection is by means of evaporative light scattering (ELSD). An evaporative light scattering detector (ELSD) atomizes the column eluate, shines light on the resulting particulate components, and detects the resulting scattered light. Theoretically, an ELSD can detect any non-volatile component. The evaporative light scattering detection of a non-chromogenic compound is based on nebulization of the HPLC eluant and evaporation of mobile-phase solvents to produce atomizing solute particles for light scattering detection. This nebulization and solvent evaporation process to produce atomizing analyte solute particles is comparable to the electrospray LC/MS procedure. Typically, the ELSD detection is compatible with electrospray LC/MS.

Implementation of an HPC method with ELSD detection that is compatible with electrospray LC/MS application involves post-column addition of a volatile solvent to enhance evaporation of the 100% aqueous mobile phase. The volatile solvent is typically selected from the group consisting of methanol, ethanol, isopropanol, and acetonitrile.

Accordingly, in methods according to the present invention, an electrospray tandem mass spectrometer is installed and connected on-line to an HPLC system with ELSD. Mass spectral data providing molecular information and tandem mass spectral data providing chemical structural information for each of the impurities that may be present in a preparation of dianhydrogalactitol can be collected. Mass spectroscopy in tandem with HPLC will provide molecular ion information and possible chemical structures having a molecular weight consistent with the molecular ion information for each of the observed impurities and degradation products.

In another alternative, preparative HPLC collection of specific DAG-related substance peaks, including impurities present in a preparation of DAG, can be performed.

Accordingly, one analytical method for analyzing the presence and quantity of impurities present in a preparation of dianhydrogalactitol comprises the steps of:

(1) analyzing a preparation of dianhydrogalactitol by subjecting the preparation to high performance liquid chromatography using elution with a mobile phase gradient to separate dianhydrogalactitol from dulcitol and other contaminants of the preparation; and (2) determining the relative concentration of one or more peaks resolved by high performance liquid chromatography that represent compounds other than dianhydrogalactitol itself.

The compounds other than dianhydrogalactitol itself can be at least one of: (1) dulcitol; (2) an impurity other than dulcitol; and (3) a degradation product of dianhydrogalactitol.

Typically, in one alternative, in this method, the mobile phase gradient is a gradient of sodium hydroxide.

In another alternative, in this method, the mobile phase gradient is a gradient of a combination of ammonium hydroxide and a volatile ammonium salt selected from the group consisting of ammonium formate and ammonium acetate.

Typically, in this method, detection is by evaporative light scattering. Typically, when evaporative light scattering is employed, the method further comprises the step of post-column addition of a volatile solvent to enhance evaporation of components of the mobile phase.

Typically, the present invention further comprises the step of analyzing one or more peaks eluting from the high performance liquid chromatography by electrospray tandem mass spectroscopy.

In one alternative, the present invention further comprises the step of preparative HPLC collection of at least one specific DAG-related substance peak.

If an impurity or degradation product (other than dulcitol) exists, the unknown impurity or degradation product can be identified by separation by column chromatography followed by at least one purification procedure to yield a solid unknown sample which can then be characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method. These methods are well known in the art.

In another alternative, the method comprises:

(1) analyzing a preparation of dianhydrogalactitol by subjecting the preparation to high performance liquid chromatography using elution with an isocratic mobile phase to separate dianhydrogalactitol from dulcitol and other contaminants of the preparation; and (2) determining the relative concentration of one or more peaks resolved by high performance liquid chromatography that represent compounds other than dianhydrogalactitol itself.

As in the method employing gradient elution, the compounds other than dianhydrogalactitol itself can be at least one of: (1) dulcitol; (2) an impurity other than dulcitol; and (3) a degradation product of dianhydrogalactitol.

In this alternative, the elution with the isocratic mobile phase can either be elution with sodium hydroxide or elution with a combination of ammonium hydroxide and a volatile ammonium salt selected from the group consisting of ammonium formate and ammonium acetate. If the isocratic mobile phase is sodium hydroxide, typically, the concentration of NaOH is from about 5 mM to 0.1 mM. Preferably, the concentration of NaOH is from about 2.5 mM to about 0.1 mM. More preferably, the concentration of NaOH is about 1 mM. If the isocratic mobile phase is a combination of ammonium hydroxide and a volatile ammonium salt selected from the group consisting of ammonium formate and ammonium acetate, the total concentration of the ammonium hydroxide and the volatile ammonium salt selected from the group consisting of ammonium formate and ammonium acetate is from about 5 mM to 0.1 mM. Preferably, the total concentration of the ammonium hydroxide and the volatile ammonium acetate is from about 2.5 mM to about 0.1 mM. More preferably, the total concentration of the ammonium hydroxide and the volatile ammonium salt selected from the group consisting of ammonium formate and ammonium acetate is about 1 mM. Typically, the proportion of ammonium hydroxide and the volatile ammonium salt selected from the group consisting of ammonium formate and ammonium acetate is about 50:50.

The invention is illustrated by the following example. This example is for illustrative purposes only, and is not intended to limit the invention.

Example

HPLC Analysis of Dianhydrogalactitol Preparations Employing Isocratic Sodium Hydroxide Elution The procedure described in this Example is used for determining dulcitol and related impurities in a dianhydrogalactitol drug preparation by ion exchange high performance liquid chromatography with refractive index detection.

In this procedure, the samples are prepared with dianhydrogalactitol at a target concentration of 5 mg/mL. Dulcitol, dianhydrogalactitol, and related impurities are separated using an anion exchange column (Hamilton RCX-10, 250× 4.1 mm, 7 μm), with 50 mM NaOH as isocratic mobile phase with refractive index detection. Dulcitol concentration is determined with an external reference standard and the contents of related substances are estimated using a DAG reference standard.

A suitable HPLC system and data acquisition system is an Agilent Technologies 1200 Series HPLC system or equivalent equipped with the following: Quat pump, Model G1311A or equivalent; auto sampler, Model 1329A or equivalent; RID detector, Model 1362A or equivalent; column temperature controller capable of 30±3° C.; and degasser, Model G1322 or equivalent. The column is a Hamilton RCX anion exchange column 250×4.1 mm, 7 μm, P/N 79440, or equivalent. Data acquisition is performed by a ChemStation and ChemStore Client/Server or an equivalent data system.

The following chemicals are used. Water is Milli-Q water or deionized water. Sodium hydroxide is standard purified grade. Dulcitol reference standard is of purity 99.95%. DAG reference standard is of purity 98.72%.

For the mobile phase (50 mM NaOH), 2.0 g NaOH is dissolved in 1 liter of water. The solution is filtered through an 0.45 μm filter. The mobile phase can be stored up to 1 month at room temperature. For the dulcitol reference stock solution (nominal 500 μg/mL), 25 mg of dulcitol reference standard is accurately weighed into a 50-mL volumetric flask. The dulcitol is diluted to volume with deionized water and mixed well. The prepared stock solution can be stored up to 3 days at 2-8° C. For the DAG reference stock solution (nominal 500 μg/mL), 25 mg of DAG reference standard is accurately weighed into a 50-mL volumetric flask. The DAG is diluted to volume with deionized water and mixed well. The prepared stock solution can be stored up to 3 days at 2-8° C. For the dulcitol-DAG standard solution (dulcitol 50 μg/mL+DAG 50 μg/mL; each at 1% of 5 mg/mL DAG), 1.0 ml of dulcitol stock and 1.0 ml of DAG stock are each quantitatively transferred into a 10-mL volumetric flask, diluted to volume with water and mixed well.

For DAG sample preparation from an API sample (nominal 1 mg/mL), about 25 mg of API sample of DAG is accurately weighed in a clean 25-mL volumetric flask. The DAG API sample is dissolved in approximately 5 mL of deionized water, diluted to volume with deionized water, and mixed. An aliquot of 1 to 2 mL of the test sample is transferred into an HPLC vial. Prepared samples can be stored for up to 2 days at 2-8° C.

For DAG sample preparation (nominal 5 mg/mL) for an API sample, about 50 mg of the API sample is accurately weighed into a clean 10-mL volumetric flask. The DAG API sample is dissolved in approximately 5 mL of water, diluted to volume with water, and mixed.

For DAG sample preparation from a lyophilized (40 mg/vial) sample, the sample is removed from the refrigerator in which the sample is stored and the seal removed. A volume of water of 5.0 mL is quantitatively transferred and the solution is mixed to dissolve the DAG, yielding an 8 mg/mL solution. An aliquot of 1.0 g of the reconstituted solution is diluted to 8.0 g with deionized water and mixed. A further aliquot of 1 to 2 mL of the test sample is transferred into an HPLC vial. Prepared samples can be stored for up to 2 days at 2-8° C.

For DAG sample preparation (nominal 5 mg/mL) for the drug product using lyophilized powder (40 mg/vial), the closure of the vial is cleaned and removed. The lyophilized vial is reconstituted with 8.0 mL water to yield a 5 mg/mL solution. An aliquot of 1 to 2 mL is transferred to an HPLC vial. Samples are prepared in duplicate (using two vials). Prepared samples can be stored at 2-8° C. for up to 24 hours.

For HPLC analysis, the HPLC system is turned on and the detector is allowed to warm up for at least 20 minutes. If necessary, place the HPLC mobile phase prepared as described above into the appropriate solvent inlet. The solvent line is primed with the mobile phase. The system and the column are equilibrated with HPLC mobile phase at a flow rate of 1.5 mL/min for at least 30 minutes. A sample analysis sequence is created. Once system suitability has been confirmed, a water blank is injected followed by injections of the standards and then the samples. A dulcitol-DAG standard is inserted after every 10 injections of samples and then a last bracketing standard at the end of the run. A suitable sample analysis sequence is shown in Table 1.

TABLE 1

Sample Analysis Sequence

| Description | No. of Injections |
|---|---|
| Blank (100% water) | 1 |
| System Suitability Test, Dul-DAG Standard (50 µg/mL each) | 6 |
| Blank (100% water) | 1 |
| Test Samples (DAG drug substance and/or drug product) - assay (duplicate preparations) | 2 (n ≤ 20) |
| Bracketing Standard, Dul-DAG Standard (50 µg/mL each) | 2 |
| Blank (water) | 1 |

The samples are analyzed using RID. As indicated above, a suitable column is a Hamilton RCX ion exchange column (250×4.1 mm, 7 µm), P/N 79440 or equivalent. The mobile phase is 50 mM NaOH in deionized water (isocratic elution). The flow rate is 1.5 ml/min. The column temperature is 30° C. The injection volume is 50.0 µL. Detection is by RID at 35° C. The run time is 8 minutes.

For analysis and integration of the chromatograms, the HPLC software is used. The chromatograms for the blank, the samples, and the test standards are reviewed and compared. Manual integration and assignment of some peaks may be necessary. Integration parameters such as slope sensitivity, peak width, peak height threshold value for rejection, integration type of shoulder peak, baseline, and split peak, as well as other parameters, are adjusted to obtain appropriate integration and values for these parameters are recorded and applied to all samples and standards.

Suitability of the system is assessed as follows. The six replicated injections of the dulcitol-DAG standard solution are evaluated using the chromatographic performance requirements of Table 2.

TABLE 2

Chromatographic Performance Requirements

| | |
|---|---|
| Dulcitol Retention time (RT): | ~2 min. |
| DAG Retention time (RT): | ~6 min. |
| Area Response variation % RSD: | ≤10.0% |
| Retention time variation % RSD: | ≤2.0% |

The dulcitol and DAG peak area in the bracketing standard solution injections should be 80% to 120% of the average peak area of each in previous SST injections. In case one bracketing standard fails to meet the criterion, the samples analyzed after the final passing bracketing standard should be re-analyzed.

In the analysis of the data, relative peak area=(peak area/total peak area)×100, where "peak area" is the individual peak area and "total peak area" is the sum of peak areas from all peaks.

Dulcitol concentration is calculated as indicated: Dulcitol ($C_u$, µg/mL)=Cs×mean sample peak area/mean dulcitol peak area of Dul-DAG standard injections, where Cs is dulcitol concentration in µg/mL.

Dulcitol content (wt %) in DAG drug substance or drug product is calculated as indicated: Dulcitol wt %=Cu (µg/mL)/1000/SC (mg/mL)×100%, where Cu is dulcitol concentration (µg/mL) calculated as above, and SC is sample concentration (mg/mL) as prepared for drug substance or drug product. If dulcitol is present, the weight percent of dulcitol is reported if equal to or greater than 0.05%; it is reported to the nearest 0.01%.

If an unknown or previously unidentified impurity other than dulcitol is present in the DAG preparation, its concentration is calculated as follows: Unknown impurity concentration (µg/mL)=Cs×mean sample peak area/mean DAG peak area of Dul-DAG standard injections. If present, the unknown impurity weight percent is calculated as follows: Cu (µg/mL)/1000/SC (mg/mL)×100%, where Cu=unknown concentration (µg/mL) calculated as above, and SC=sample concentration (mg/mL) as prepared in 8.2.2 for drug substance or 8.2.3 for drug product. Each unknown impurity, if present, is reported if equal to or greater than 0.05%; it is reported to the nearest 0.01%.

The assay results in weight percent are calculated for each sample and for the mean of duplicate samples.

Advantages of the Invention

The present invention provides an improved analytical method for the detection and quantitation of impurities present in dianhydrogalactitol preparations, including dulcitol and unknown impurities, as well as methods for isolation and identification of unknown impurities present in dianhydrogalactitol preparations. The methods of the present invention allow the large-scale preparation of dianhydrogalactitol of high purity suitable for pharmaceutical use and reduce the possibility of significant side effects caused by the presence of impurities in dianhydrogalactitol preparations intended for pharmaceutical use.

Methods according to the present invention possess industrial applicability for analysis of dianhydrogalactitol preparations and determination and quantitation of impurities in dianhydrogalactitol preparations.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. An analytical method for analyzing the presence and quantity of impurities present in a preparation of dianhydrogalactitol comprising the steps of:
    (a) analyzing a preparation of dianhydrogalactitol by subjecting the preparation to high performance liquid chromatography using elution with a mobile phase gradient to separate dianhydrogalactitol from dulcitol and other contaminants of the preparation; and
    (b) determining the relative concentration of one or more peaks resolved by high performance liquid chromatography that represent compounds other than dianhydrogalactitol itself.

2. The method of claim 1 wherein the compounds other than dianhydrogalactitol itself are at least one of: (1) dulcitol; (2) an impurity other than dulcitol; and (3) a degradation product of dianhydrogalactitol.

3. The analytical method of claim 1 wherein elution is with a gradient of NaOH from about 2.5 mM to about 0.1 mM.

4. The analytical method of claim 3 wherein elution is with a gradient of NaOH from about 1.5 mM to about 0.1 mM.

5. The analytical method of claim 4 wherein elution is with a gradient of NaOH from about 1 mM to about 0.1 mM.

6. The analytical method of claim 1 wherein elution is with a gradient of a combination of ammonium hydroxide and a volatile ammonium salt selected from the group consisting of ammonium formate and ammonium acetate and the total concentration of the ammonium hydroxide and the volatile ammonium salt selected from the group consisting of ammonium formate and ammonium acetate is from about 2.5 mM to about 0.1 mM.

7. The analytical method of claim 6 wherein the total concentration of the ammonium hydroxide and the volatile ammonium salt selected from the group consisting of ammonium formate and ammonium acetate is from about 1.5 mM to about 1.0 mM.

8. The analytical method of claim 7 wherein the total concentration of the ammonium hydroxide and the volatile ammonium salt selected from the group consisting of ammonium formate and ammonium acetate is from about 1.0 mM to about 0.1 mM.

9. The analytical method of claim 4 wherein the proportion of ammonium hydroxide and the volatile ammonium salt selected from the group consisting of ammonium formate and ammonium acetate is varied from about 100:1 at the beginning of elution to about 1:100 at the end of elution.

10. The analytical method of claim 1 wherein the step of determining the relative concentration of one or more peaks resolved by high performance liquid chromatography that represent compounds other than dianhydrogalactitol itself is performed by evaporative light scattering detection.

11. The analytical method of claim 10 wherein the evaporative light scattering detection is compatible with electrospray LC/MS.

12. An analytical method for analyzing the presence and quantity of impurities present in a preparation of dianhydrogalactitol comprising the steps of:
    (a) analyzing a preparation of dianhydrogalactitol by subjecting the preparation to high performance liquid chromatography using elution with a mobile phase gradient to separate dianhydrogalactitol from dulcitol and other contaminants of the preparation; and
    (b) determining the relative concentration of one or more peaks resolved by high performance liquid chromatography that represent compounds other than dianhydrogalactitol itself;
wherein the step of determining the relative concentration of one or more peaks resolved by high performance liquid chromatography that represent compounds other than dianhydrogalactitol itself is performed by evaporative light scattering detection; and
wherein the evaporative light scattering detection comprises post-column addition of a volatile solvent to enhance evaporation of the 100% aqueous mobile phase.

13. The analytical method of claim 12 wherein the volatile solvent is selected from the group consisting of methanol, ethanol, isopropanol, and acetonitrile.

14. The analytical method of claim 1 wherein an electrospray tandem mass spectrometer is installed and connected on-line to an HPLC system with ELSD.

15. The analytical method of claim 14 wherein tandem mass spectral data providing chemical information for each of the impurities and degradation products that may be present in a preparation of dianhydrogalactitol is collected.

16. The analytical method of claim 15 wherein the mass spectroscopy in tandem with HLPC provides molecular ion information and possible chemical structures having a molecular weight consistent with the molecular ion information for each of the observed impurities and degradation products.

17. The analytical method of claim 15 wherein at least one impurity or degradation product is identified by separation by column chromatography followed by at least one purification procedure to yield a solid unknown sample.

18. The analytical method of claim 17 wherein the solid unknown sample is characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method.

19. The analytical method of claim 1 further comprising the step of performing preparative HPLC collection of at least one specific substance peak present in a preparation of dianhydrogalactitol.

20. The analytical method of claim 19 wherein the at last one substance peak present in the preparation of dianhydrogalactitol is an impurity.

21. The analytical method of claim 19 wherein the at last one substance peak present in the preparation of dianhydrogalactitol is a degradation product.

22. An analytical method for analyzing the presence and quantity of impurities present in a preparation of dianhydrogalactitol comprising the steps of:
(a) analyzing a preparation of dianhydrogalactitol by subjecting the preparation to high performance liquid chromatography using elution with an isocratic mobile phase to separate dianhydrogalactitol from dulcitol and other contaminants of the preparation; and
(b) determining the relative concentration of one or more peaks resolved by high performance liquid chromatography that represent compounds other than dianhydrogalactitol itself.

23. The analytical method of claim 22 wherein the compounds other than dianhydrogalactitol itself are at least one of: (1) dulcitol; (2) an impurity other than dulcitol; and (3) a degradation product of dianhydrogalactitol.

24. The analytical method of claim 22 wherein the isocratic mobile phase is NaOH, and the concentration of NaOH is from about 5 mM to about 0.1 mM.

25. The analytical method of claim 24 wherein the concentration of NaOH is from about 2.5 mM to about 0.1 mM.

26. The analytical method of claim 25 wherein the concentration of NaOH is about 1 mM.

27. The analytical method of claim 22 wherein the isocratic mobile phase is a combination of ammonium hydroxide and a volatile ammonium salt selected from the group consisting of ammonium formate and ammonium acetate and the total concentration of the ammonium hydroxide and the volatile ammonium salt selected from the group consisting of ammonium formate and ammonium acetate is from about 5 mM to about 0.1 mM.

28. The analytical method of claim 27 wherein the total concentration of the ammonium hydroxide and the volatile ammonium salt selected from the group consisting of ammonium formate and ammonium acetate is from about 2.5 mM to about 0.1 mM.

29. The analytical method of claim 28 wherein the total concentration of the ammonium hydroxide and the volatile ammonium salt selected from the group consisting of ammonium formate and ammonium acetate is about 1 mM.

30. The analytical method of claim 27 wherein the proportion of ammonium hydroxide and the volatile ammonium salt selected from the group consisting of ammonium formate and ammonium acetate is about 50:50.

31. The analytical method of claim 22 wherein the step of determining the relative concentration of one or more peaks resolved by high performance liquid chromatography that represent compounds other than dianhydrogalactitol itself is performed by evaporative light scattering detection.

32. The analytical method of claim 31 wherein the evaporative light scattering detection is compatible with electrospray LC/MS.

33. An analytical method of claim 32 comprising the steps of:
(a) analyzing a preparation of dianhydrogalactitol by subjecting the preparation to high performance liquid chromatography using elution with an isocratic mobile phase to separate dianhydrogalactitol from dulcitol and other contaminants of the preparation; and
(b) determining the relative concentration of one or more peaks resolved by high performance liquid chromatography that represent compounds other than dianhydrogalactitol itself;
wherein the step of determining the relative concentration of one or more peaks resolved by high performance liquid chromatography that represent compounds other than dianhydrogalactitol itself is performed by evaporative light scattering detection, wherein the evaporative light scattering detection is compatible with electrospray LC/MS; and
wherein the evaporative light scattering detection comprises post-column addition of a volatile solvent to enhance evaporation of the 100% aqueous mobile phase.

34. The analytical method of claim 33 wherein the volatile solvent is selected from the group consisting of methanol, ethanol, isopropanol, and acetonitrile.

35. The analytical method of claim 22 wherein an electrospray tandem mass spectrometer is installed and connected on-line to an HPLC system with ELSD.

36. The analytical method of claim 25 wherein tandem mass spectral data providing structural information for each of the impurities that may be present in a preparation of dianhydrogalactitol is collected.

37. The analytical method of claim 36 wherein the mass spectroscopy in tandem with HLPC provides molecular ion information and possible chemical structures having a molecular weight consistent with the molecular ion information for each of the observed impurities and degradation products.

38. The analytical method of claim 36 wherein at least one impurity or degradation product is identified by separation by column chromatography followed by at least one purification procedure to yield a solid unknown sample.

39. The analytical method of claim 38 wherein the solid unknown sample is characterized for identification by at least one standard analytical procedure selected from the group consisting of nuclear magnetic resonance (NMR), mass spectroscopy (MS), Fourier transform infrared spectroscopy (FT-IR), elemental analysis, determination of purity by HPLC, and determination of water content by the Karl Fischer titration method.

40. The analytical method of claim 1 further comprising the step of performing preparative HPLC collection of at least one specific substance peak present in a preparation of dianhydrogalactitol.

41. The analytical method of claim 40 wherein the at last one substance peak present in the preparation of dianhydrogalactitol is an impurity.

42. The analytical method of claim 40 wherein the at last one substance peak present in the preparation of dianhydrogalactitol is a degradation product.

* * * * *

UNITED STATES PATENT AND TRADEMARK OFFICE
CERTIFICATE OF CORRECTION

PATENT NO.        : 10,145,824 B2
APPLICATION NO.   : 14/380924
DATED             : December 4, 2018
INVENTOR(S)       : Liu Page 1 of 1

It is certified that error appears in the above-identified patent and that said Letters Patent is hereby corrected as shown below:

In the Claims

Column 13    Line 24        "at last one" should read --at least one--
(Claim 20, Line 1)

Column 13    Line 27        "at last one" should read --at least one--
(Claim 21, Line 1)

Column 14    Line 16        "method of claim 32 comprising" should read
(Claim 33, Line 1)          --method comprising--

Column 15    Line 1         "at last one" should read --at least one--
(Claim 41, Line 1)

Column 15    Line 4         "at last one" should read --at least one--
(Claim 42, Line 1)

Signed and Sealed this
Eleventh Day of February, 2020

Andrei Iancu
*Director of the United States Patent and Trademark Office*